(12) United States Patent
Buzot

(10) Patent No.: US 6,533,748 B2
(45) Date of Patent: *Mar. 18, 2003

(54) TAMPON APPLICATOR WITH ROUNDED RECESS

(75) Inventor: Herve Buzot, North Brunswick, NJ (US)

(73) Assignee: Johnson & Johnson GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/454,989

(22) Filed: Dec. 3, 1999

(65) Prior Publication Data

US 2001/0049487 A1 Dec. 6, 2001

(30) Foreign Application Priority Data

Dec. 3, 1998 (DE) .......................... 198 56 639

(51) Int. Cl.⁷ ................................................ A61F 13/20
(52) U.S. Cl. ...................................................... 604/15
(58) Field of Search ...................... 604/11–18, 285–288, 604/57, 59, 60, 311

(56) References Cited

U.S. PATENT DOCUMENTS

| | | | |
|---|---|---|---|
| 2,711,173 A | | 6/1955 | Seidler |
| 2,879,770 A | | 3/1959 | Graham, Jr. |
| 3,086,527 A | * | 4/1963 | Forrest .......................... 604/15 |
| 3,757,781 A | * | 9/1973 | Smart .......................... 604/59 |
| 4,060,083 A | * | 11/1977 | Hanson ........................ 604/59 |
| 4,453,930 A | * | 6/1984 | Child ........................... 604/59 |
| 4,536,178 A | * | 8/1985 | Lichstein et al. .............. 604/15 |
| 5,310,407 A | * | 5/1994 | Casale .......................... 604/51 |
| 5,474,535 A | * | 12/1995 | Place et al. .................... 604/60 |
| 6,248,089 B1 | * | 6/2001 | Porat ........................... 604/17 |

FOREIGN PATENT DOCUMENTS

| | | |
|---|---|---|
| CH | 614378 | 11/1979 |
| DE | 197 58 376 A | 7/1999 |
| EP | 0 723 768 A2 | 7/1996 |
| GB | 530318 | 6/1939 |
| WO | 99/33429 | 8/1999 |

OTHER PUBLICATIONS

PCT International Search Report (PCT/EP99/09755).

* cited by examiner

Primary Examiner—Dennis Ruhl

(57) ABSTRACT

The invention relates to a tampon applicator, comprising an elongated outer cylinder, a tampon contained therein and a plunger by which the tampon can be pushed out through a forward delivery opening of the outer cylinder. In order to facilitate handling the applicator is, on the rearward end, opposite to the delivery opening (12), provided with a recess (6) extending perpendicular to the longitudinal axis of the applicator, the cross-sectional contour of the recess (6) being shaped to receive a finger in a finger seat.

9 Claims, 1 Drawing Sheet

TAMPON APPLICATOR WITH ROUNDED RECESS

FIELD OF THE INVENTION

The invention relates to an applicator type tampon having an elongated outer cylinder, a tampon contained therein and a plunger by which the tampon can be pushed out through a forward delivery opening of the outer cylinder.

BACKGROUND OF THE INVENTION

A simple applicator of this type is for example described in Sakurai et al., U.S. Pat. No. 4,269,187. This tampon applicator comprises an outer cylinder which holds in its interior a tampon near its forward end portion. An absorbent material push-out portion is inserted through a rearward opening of the outer cylinder and is slidable therein. When sliding the push-out portion forward, its front end abuts against the rearward end of the tampon, whereby the tampon, upon further advancing the push-out portion, is pushed through the delivery opening out of the outer cylinder. The push-out portion presents, at its rearward end, a planar cover onto which the user presses with her finger to thereby advance the push-out portion while holding the outer cylinder with her other fingers.

Another applicator-type tampon is disclosed in Sakurai, U.S. Pat. No. 4,273,125. This device includes an outer cylinder for enclosing the tampon and a pusher structure. The pusher structure has a cylinder and a pair of push-out pieces projecting therefrom in the shape of segments of the original cylinder wall. At a position spaced from the insertion end, the outer cylinder is provided with holes. These holes are also located behind the rearward end of the tampon when the latter is in its initial position in the outer cylinder. Before use the pusher structure is positioned with its push-out pieces engaging the outer wall of the outer cylinder and with its cylindrical end portion being located behind the rearward end of the outer cylinder. To use the applicator the pusher structure is first pulled back until the front ends of said elongated bars are in registration with the openings in the outer cylinder. Then, the forward, ends of the bars are introduced into the openings and slid into the interior of the outer cylinder by pushing the pusher structure forward. By further advancing the pusher structure, the tampon is then pushed through the delivery opening out of the outer cylinder. The rearward end surface of the pusher structure onto which a finger has to press to advance the pusher cylinder, appears to have a flat supporting surface.

A disadvantage of these prior art applicators is that the handling is difficult and uncomfortable since the finger which has to rest on the rearward end of the applicator can easily slide off the end surface, in particular since the applicator is usually handled with one hand.

What is needed is a tampon applicator which can easily be handled and which allows to push out the tampon in an easy and safe way.

SUMMARY OF THE INVENTION

According to the present invention the applicator is, on its rearward end opposite to the delivery opening, provided with a recess extending perpendicular to the longitudinal axis of the applicator, the cross-sectional contour of the recess being shaped to receive a finger. The recess can for example have the shape of a cylinder segment. Such a recess for receiving or seating the finger allows the user to hold the applicator at the rearward end with one finger in a secure manner, without risk that the finger could slide off when using the applicator.

DETAILED DESCRIPTION OF THE PREFERRED EMBODIMENTS

Figure 1:
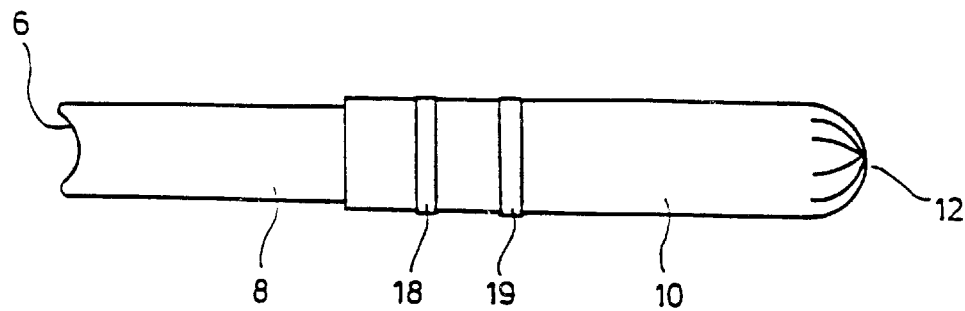
FIG. 1: shows a side plan view of a first embodiment of a tampon applicator.

FIG. 1 shows a first embodiment of the tampon applicator in its initial position, before use, as it is removed from its package. The tampon applicator comprises an outer cylinder 10 having a cylindrical hollow interior into which a tampon is inserted. Into the rearward end of the outer cylinder 10 an inner cylinder 8 is inserted which is slidably movable within the outer cylinder 10. In the forward end of the outer cylinder 10 a delivery opening 12 is provided through which the tampon is pushed out from the interior of the outer cylinder 10 when the inner cylinder 8 is pushed forward in the direction to the delivery opening 12.

The rearward end of the inner cylinder 8 is provided with a curvilinear recess 6 having the shape of a flute or groove extending perpendicular (in the representation of FIG. 1 extending perpendicular to the paper plane) to the longitudinal axis of the applicator. This flute- or groove-shaped recess 6 has, as illustrated in FIG. 1, a cross-sectional contour which provides for a comfortable and slide-free seat and support of a finger. The shape of the recess can be generally described as a cylinder segment shape.

The recess 6 for supporting a finger allows for example that the index finger of the user is received and supported therein and pushes the inner cylinder 8 forward while the outer cylinder 10 is held with other fingers, wherein the user does not have to pay particular attention to the proper positioning of the index finger on the inner cylinder while pushing it forward, but the finger remains, received in the recess 6, properly positioned in the finger seat. To further improve the handling of the applicator the outer surface of the outer cylinder 10 is provided with at least one raised element, for example two circumferential rings or flanges 18, 19, which allow the user to hold the outer cylinder between two fingers, without any danger of the cylinder sliding in longitudinal direction.

The applicator can be made of plastic, biodegradable material or cardboard. In particular plastic materials such as polyethylene, polypropulene, polyurethane, polyesters, ethylene-vinyl acetate, polystyrene can be used to form the applicator of the invention. Biodegradable materials which can be used to form the applicator of the invention are for example described in EP 0 606 923 A1; suitable biodegradable materials are for example poly(vinyl alcohol), polyoxyethylene, and the like. The inner cylinder can be formed as a solid or hollow cylinder. In case of a hollow cylinder the recess 6 is formed by two opposite indentations in the rearward end of the wall surface of the inner cylinder 8.

Figure 2:
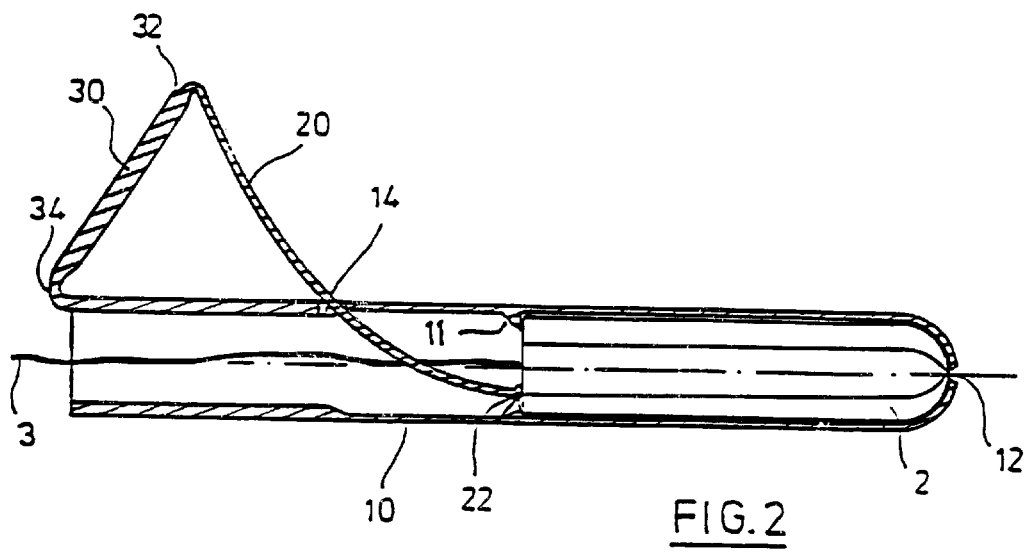
FIG. 2: shows a side cross-sectional view of a second embodiment of the tampon applicator.
Figure 3:
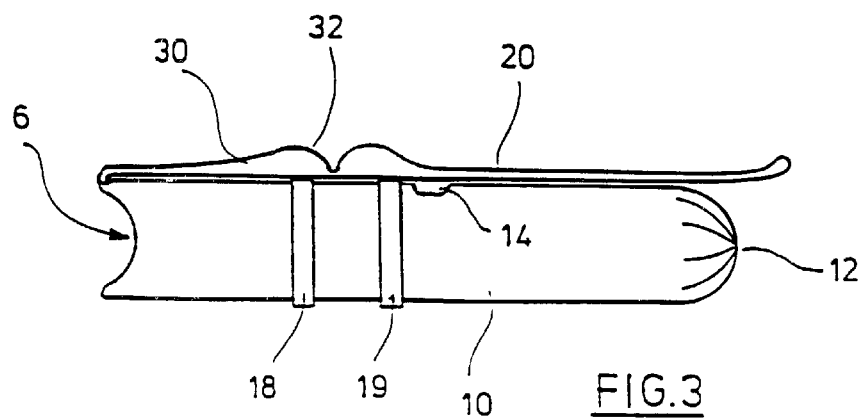
FIG. 3: shows a side plan view of the tampon applicator of FIG. 2.

In FIGS. 2 and 3 a second embodiment of the invention is shown, in FIG. 2 the applicator being illustrated in a cross-sectional view and in FIG. 3 in a side plan view. In the embodiment illustrated in FIGS. 2 and 3 the tampon applicator is not formed with an inner cylinder but with a pusher member which comprises a push lever 30 and a pusher element 20. This type of applicator tampon is more fully described in Buzot, U.S. Ser. No. 09/331,907, herein incorporated by reference. In the following the construction and function of this tampon applicator is described with reference to FIG. 2.

The tampon 2 having a withdrawal string 3 is positioned within the interior of the outer cylinder 10 so that the front end portion of the tampon 2 is located adjacent to the delivery opening 12 of the outer cylinder 10. Stops 11 on the inner wall of the outer cylinder 10 are provided to prevent the tampon from moving backward from its initial position adjacent the delivery opening 12.

The outer cylinder 10 is provided with a push lever 30 which is with one of its ends 34 pivotally connected to the exterior of the outer cylinder. At its other end 32 the push lever 30 is pivotally connected to an elongated pusher element 20. An opening 14 is provided in the outer wall of the outer cylinder 10. Through this opening 14 the elongated pusher element 20 can be, with its front end portion 22 leading, slid into the interior of the outer cylinder 10. The opening 14 is located in longitudinal direction between the rear end 3 of the tampon 2 and the rear end 34 of the push lever 30 which is pivotally connected to the outer cylinder 10. The opening 14 can be located in longitudinal direction between the rear end 3 of the tampon 2 and the forward end 32 of the push lever 30, in particular the opening 14 can be, as in the illustrated embodiments, located at the position of the forward end 32 of the push lever 30 when the latter is folded against the outer cylinder 10.

The outer cylinder 10, the push lever 30 and the pusher element 20 can be integrally formed as a single piece, wherein the pivotal connections between the outer cylinder 10 and the push lever 30 at its end 34 and between the pusher element 20 and the push lever at its end 32 are realized by zones of weakened material. The push lever 30 is, as illustrated, preferably thicker than the push element 20 in order to have more rigidity so that the user can safely press on it and the force is transmitted to the pusher element 20 essentially without bending of the push lever 30.

In order to use the tampon applicator the push lever 30 which is shown in FIG. 3 in its initial or start position is pivoted away from the outer surface of the outer cylinder 10, and the tip 22 of the pusher element 20 is inserted into the opening 14 in the cylinder wall.

Then, by further turning the push lever 30 towards the outer surface of the outer cylinder the pusher element 20 is being slid further into the interior of the outer cylinder 10, until it contacts the rearward end 3 of the tampon 2. This position is shown in FIG. 2. In this position the applicator is ready for use, and can be introduced into the vagina. Thereafter the push lever 30 is further turned towards the outer surface of the outer cylinder 10 with the thumb of the user pressing onto the push lever 30 to further turn the push lever. By further turning the push lever 30 the pusher element 20 is advanced into the interior of the outer cylinder 10, thereby advancing the tampon 2 and pushing it out of the delivery opening 12 of the outer cylinder 10.

The outer cylinder 10 is provided with two circumferential rings or flanges 18, 19 which allow the user to grip the applicator between two fingers between the rings 18 and 19, without any danger that the applicator could slide away in longitudinal direction between the fingers.

In the position as illustrated in FIG. 2 and during the further movement the elongated pusher element 20 does not extend along a straight line but undergoes a certain bending along its longitudinal axis. After inserting the pusher element 30 through the opening 14 and further advancing the pusher element, it finally contacts the inner wall of the outer cylinder 10 in area opposite to the opening 14, whereupon the pusher element slightly bends during its progressing movement in the general direction of the longitudinal axis of the outer cylinder. This flexibility or capability of bending is easily achievable if the pusher element is, as illustrated, formed by a simple rod, the diameter of which can be dimensioned to achieve the desired flexibility. When making the pusher element of plastic or cardboard the required flexibility is easily achievable.

In the plan view of FIG. 3 it can be seen that the tampon applicator is provided at its rearward end with a recess 6 for receiving a finger. The recess 6 is formed at the rearward end, opposite to the delivery opening 12 on the outer cylinder 10. The recess 6 has a flute- or groove-shaped cross-sectional contour so that a finger is securely and comfortably supported therein.

The specification is presented to aid in the complete and non-limiting understanding of the invention disclosed herein. Since many variations and embodiments of the invention can be made without departing from its spirit and scope, the invention resides in the claims hereinafter appended.

What is claimed is:

1. Tampon applicator comprising an elongated outer cylinder comprising a rearwardly open sleeve defined by a sleeve wall that is suitable for containing an absorbent tampon and a plunger by which the absorbent tampon can be pushed out through a forward delivery opening of the outer cylinder, wherein the applicator is, on a rearward end, opposite to the forward delivery opening, provided with a recess extending perpendicular to the longitudinal axis of the applicator, the recess having a cross-sectional contour shaped to receive a finger comprising two opposite indentations in the sleeve wall and wherein the plunger is arranged and configured to be introduced through an opening in an outer wall of the outer cylinder.

2. Tampon applicator according to claim 1, wherein the recess is shaped when viewed in plan view, as an arc of a circle.

3. Tampon applicator according to claim 1, wherein the outer cylinder has an outer surface that has at least one raised element adapted to avoid longitudinal movement of the applicator when it is gripped between two fingers.

4. Tampon applicator according to claim 1, wherein the at least one raised element comprises a pair of raised circumferential rings.

5. A tampon applicator, comprising an elongated outer cylinder suitable for containing an absorbent tampon and a plunger comprising a rearwardly open sleeve defined by a sleeve wall by which the absorbent tampon can be pushed out through a forward delivery opening of the outer cylinder, wherein the plunger is, on a rearward end, opposite to the delivery opening, provided with a recess extending perpendicular to the longitudinal axis of the applicator, the recess having cross-sectional contour shaped to receive a finger comprising two opposite indentations in the sleeve wall.

6. Tampon applicator according to claim 5, wherein the outer cylinder has an outer surface that has at least one raised element adapted to avoid longitudinal movement of the applicator when it is gripped between two fingers.

7. Tampon applicator according to claim 6, wherein the at least one raised element comprises a pair of raised circumferential rings.

8. Tampon applicator comprising an elongated outer cylinder having at least one raised element adapted to avoid longitudinal movement of the applicator when it is gripped between two fingers and being suitable for containing an absorbent catamenial tampon for the purpose of being inserted into the vagina and a hollow plunger comprising a rearwardly open sleeve defined by a sleeve wall by which the absorbent tampon can be pushed out through a forward delivery opening of the outer cylinder, wherein the plunger is, on a rearward end, opposite to the forward delivery opening of the outer cylinder, provided with a recess having a shape of a groove extending perpendicular to the longitudinal axis of the applicator, the recess having a cross-sectional contour shaped to receive a finger comprising two opposite indentations in the sleeve wall.

9. Tampon applicator according to claim 8, wherein the at least one raised element comprises a pair of raised circumferential rings.

\* \* \* \* \*